(12) United States Patent
Carr-Jordan et al.

(10) Patent No.: US 10,736,555 B2
(45) Date of Patent: Aug. 11, 2020

(54) WEARABLE MOOD AND ACTIVITY MONITORING SYSTEM

(71) Applicants: Erin Marie Carr-Jordan, Chandler, AZ (US); Annissa D. Furr, Peoria, AZ (US)

(72) Inventors: Erin Marie Carr-Jordan, Chandler, AZ (US); Annissa D. Furr, Peoria, AZ (US)

(*) Notice: Subject to any disclaimer, the term of this patent is extended or adjusted under 35 U.S.C. 154(b) by 10 days.

(21) Appl. No.: 16/148,771

(22) Filed: Oct. 1, 2018

(65) Prior Publication Data

US 2019/0029584 A1    Jan. 31, 2019

Related U.S. Application Data

(63) Continuation-in-part of application No. 14/941,635, filed on Nov. 15, 2015, now abandoned.

(51) Int. Cl.
*A61B 5/00* (2006.01)
*A61B 5/16* (2006.01)
(Continued)

(52) U.S. Cl.
CPC ............ *A61B 5/165* (2013.01); *A61B 5/1118* (2013.01); *A61B 5/167* (2013.01); *A61B 5/6824* (2013.01); *A61B 5/6831* (2013.01); *G06F 1/163* (2013.01); *G06F 3/014* (2013.01); *G06F 3/015* (2013.01); *G06F 3/03547* (2013.01); *G06F 3/04817* (2013.01); *G06N 5/00* (2013.01); *G06Q 10/101* (2013.01); *G06Q 50/01* (2013.01); *G16H 20/70* (2018.01); *G16H 40/63* (2018.01); *G16H 40/67* (2018.01); *G16H 80/00* (2018.01); *H04W 4/029* (2018.02); *A61B 5/0022* (2013.01); *A61B 5/16* (2013.01); *A61B 5/486* (2013.01); *A61B 5/4806* (2013.01); *A61B 5/681* (2013.01); *G06F 3/0482* (2013.01); *G06F 2203/011* (2013.01)

(58) Field of Classification Search
None
See application file for complete search history.

(56) References Cited

U.S. PATENT DOCUMENTS

| | | | | |
|---|---|---|---|---|
| 7,334,711 B1 * | 2/2008 | Winters | ................... | A45F 5/00 224/217 |
| 8,725,842 B1 * | 5/2014 | Al-Nasser | .............. | G04G 17/08 709/219 |
| 8,851,372 B2 * | 10/2014 | Zhou | ....................... | G06F 1/163 235/380 |
| 9,288,836 B1 * | 3/2016 | Clement | ................ | H04W 84/18 |
| 9,563,234 B2 * | 2/2017 | Popalis | ................... | G06F 1/163 |

(Continued)

*Primary Examiner* — Sunit Pandya

(57) ABSTRACT

The present invention is a wearable mood and activity monitoring system comprising a wrist worn device, further comprising an adjustable wrist band and a health monitoring assembly further comprising a faceplate with an interactive touchscreen display, a microchip processor in wired communication via a plurality of circuitry cables with a health sensor for detecting real-time physiological data of the user, an accelerometer, a tracking system for tracking a relative location of the user, an information receiver and transmitter unit, and a power source, a plate securer, and a backplate; and a remote monitoring device. The user selects a user-reported mood using the interactive touchscreen display. The health sensor generates the real-time physiological data of the user. The microchip processor is configured to evaluate the real-time physiological data with the user-reported mood to provide an overall mental health of the user.

19 Claims, 6 Drawing Sheets

(51) Int. Cl.
| | |
|---|---|
| *H04W 4/029* | (2018.01) |
| *G16H 80/00* | (2018.01) |
| *G06F 1/16* | (2006.01) |
| *G06Q 10/10* | (2012.01) |
| *G06Q 50/00* | (2012.01) |
| *A61B 5/11* | (2006.01) |
| *G06F 3/0354* | (2013.01) |
| *G16H 40/67* | (2018.01) |
| *G06N 5/00* | (2006.01) |
| *G16H 40/63* | (2018.01) |
| *G06F 3/0481* | (2013.01) |
| *G06F 3/01* | (2006.01) |
| *G16H 20/70* | (2018.01) |
| *G06F 3/0482* | (2013.01) |

(56) References Cited

U.S. PATENT DOCUMENTS

| | | | |
|---|---|---|---|
| 9,568,891 B2 * | 2/2017 | Adams | G04G 21/08 |
| 2001/0017663 A1 * | 8/2001 | Yamaguchi | H04N 1/00249 |
| | | | 348/373 |
| 2008/0054039 A1 * | 3/2008 | Wulff | A45F 5/00 |
| | | | 224/575 |
| 2014/0143064 A1 * | 5/2014 | Tran | A61B 5/0022 |
| | | | 705/14.66 |
| 2014/0322677 A1 * | 10/2014 | Segal | G09B 5/02 |
| | | | 434/107 |
| 2015/0015502 A1 * | 1/2015 | Al-Nasser | G04G 17/08 |
| | | | 345/173 |
| 2015/0170115 A1 * | 6/2015 | Lacek | G06Q 30/0226 |
| | | | 705/39 |
| 2016/0379511 A1 * | 12/2016 | Dawson | G06F 3/04847 |
| | | | 434/362 |

\* cited by examiner

WEARABLE MOOD AND ACTIVITY MONITORING SYSTEM

CROSS REFERENCE TO RELATED APPLICATION

The present application is a Continuation-in-Part of application Ser. No. 14/941,635 filed Nov. 15, 2015 entitled "WEARABLE COMPUTING DEVICE FOR YOUTH AND DEVELOPMENTALLY DISABLED", the contents of which are incorporated herein by this reference in their entirety and are not admitted to be prior art with respect to the present invention by the mention in this cross-reference section.

FIELD OF THE INVENTION

The present invention relates generally to the field of wearable computing devices. In particular, the present invention relates to a wearable device that allows a user to report their mood and tracks physical activity. The wearable mood and activity monitoring system tracks that information and provides instruction to the user and transmits that information to a parent, guardian, or caregiver.

BACKGROUND OF THE INVENTION

Generally, parents and other caregivers are dependent on second hand information and guesswork rather than real-time actionable data that can be used to improve the health and wellbeing outcomes for their kids.

Additionally, mental health issues in youth are on the rise. Youth are increasingly diagnosed with anxiety, depression, and other behavior anomalies including attention deficits, hyperactivity, stress disorders, oppositional behavior, reactivity, and aggression. Further, autism and autism spectrum diagnosis rise each year as do the numbers of children categorized as overweight or obese. Increasing numbers of youth experience poor performance and truancy in school. The prevalence of social media use by youth compounding poorly developed interpersonal skills, negatively impacts self-esteem and body image, and can negatively impact sleep. Identifying patterns in activity and mood can lead to early discovery of potential problems and correlations and can provide valuable insight into the connections between mental health and physical health. In order to achieve measurable results, it is essential to examine patterns of behavior and activity in combination. The present invention will provide a comprehensive report of physical activity, sleep patterns, and mood changes over time.

In general, youth communicate differently than their adult parents and caregivers. For kids and teens, emojis can be the gateway to aspects of communication previously closed to them, such as active participation in emotional well-being, self-awareness, and being heard in educational and care settings. Further, kids with special needs have a tendency to wander. This wandering leads to risky behavior and according to awaare.org, 49% of children with autism "engage in elopement behavior with a substantial number at risk for bodily harm".

Additionally, youth need motivation as they develop healthy habits that include physical activity and awareness. It is indisputable that an increase in physical activity impacts youth in both a mental and a physical capacity. Currently, the U.S. is facing a childhood obesity epidemic. Being overweight or obese in childhood is associated with $14.1 billion in additional prescription drug, emergency room, and out-patient visit healthcare costs annually. The present invention solves the problems above by providing a wearable device with an interactive touch screen display that tracks a user-reported mood along with physical activity levels. This allows users to take an active role in tracking physical activity and allows the wearer and caregiver to set unique goals that are most beneficial to the individual wearer.

It is well known that exercise and other physical activity can improve mood and mental health. For example, exercise and physical activity has been shown to have positive effects on stress, depression, and anxiety to name a few. In addition, psychological mechanisms influence the effects of exercise on mood states. Exercise has also been shown to reduce inflammation via several different processes (inflammation, cytokines, toll-like receptors, adipose tissue and via the vagal tone), which can contribute to better health outcomes in people suffering from mood disorders. The present invention correlates physiological data with a user-reported mood to provide an overall mental health of the user.

Any discussion of prior art throughout the specification should in no way be considered as an admission that such prior art is widely known or forms part of the common general knowledge in the field.

BRIEF SUMMARY OF THE INVENTION

According to the present invention there is provided a wearable mood and activity monitoring system configured to monitor an overall mental health of a user comprising: a wrist worn device, further comprising an adjustable wrist band for attaching said wrist worn device to a wrist of a user; a health monitoring assembly; and a remote monitoring device.

The health monitoring assembly further comprises in functional combination a faceplate further comprising an interactive touchscreen display, a microchip processor in wired communication via a plurality of circuitry cables with at least one health sensor for detecting real-time physiological data of the user, at least one accelerometer, at least one tracking system for tracking a relative location of the user, at least one information receiver and transmitter unit, and at least one power source.

The health monitoring assembly is preferably configured to couple to a backplate using at least one plate securer. Preferably the user provides an input using the interactive touchscreen display to select a user-reported mood. In addition, the at least one health sensor is installed to the backplate such that the at least one health sensor is in contact with a radial artery of the user for generating the real-time physiological data of the user. The at least one microchip processor preferably further comprises a data processing means for evaluating the real-time physiological data and the user-reported mood to provide an overall mental health condition of the user. The at least one remote monitoring device is configured to automatically receive the real-time physiological data and the user-reported mood by the wrist worn device for alerting a caregiver of the overall mental health of the user.

The wrist worn device preferably further comprises a clock processor to track current time data. The health monitoring system is preferably configured to prompt the user to select a user-reported mood by using the interactive touchscreen display, where the prompt could be based on the physiological data. The wrist worn device is preferably waterproof via a watertight seal located between the backplate and the faceplate of the wrist worn device. The user-reported mood is preferably selected using a plurality of pictographs depicting various moods displayed on the interactive touchscreen display. The data processing means preferably combines said user-reported mood with said physiological data to communicate with said caregiver using trends over time. The user-reported mood is preferably combined with said physiological data to output instructions to the caregiver and/or the user.

BRIEF DESCRIPTION OF THE DRAWINGS

The preferred embodiment of the present invention will now be described, by way of example only, with reference to the accompanying drawings in which.

DETAILED DESCRIPTION OF THE INVENTION

The foregoing and other objectives, features, and advantages of the invention will be more readily understood upon consideration of the following description of the invention taken in conjunction with the accompanying drawings.

Figure 1:
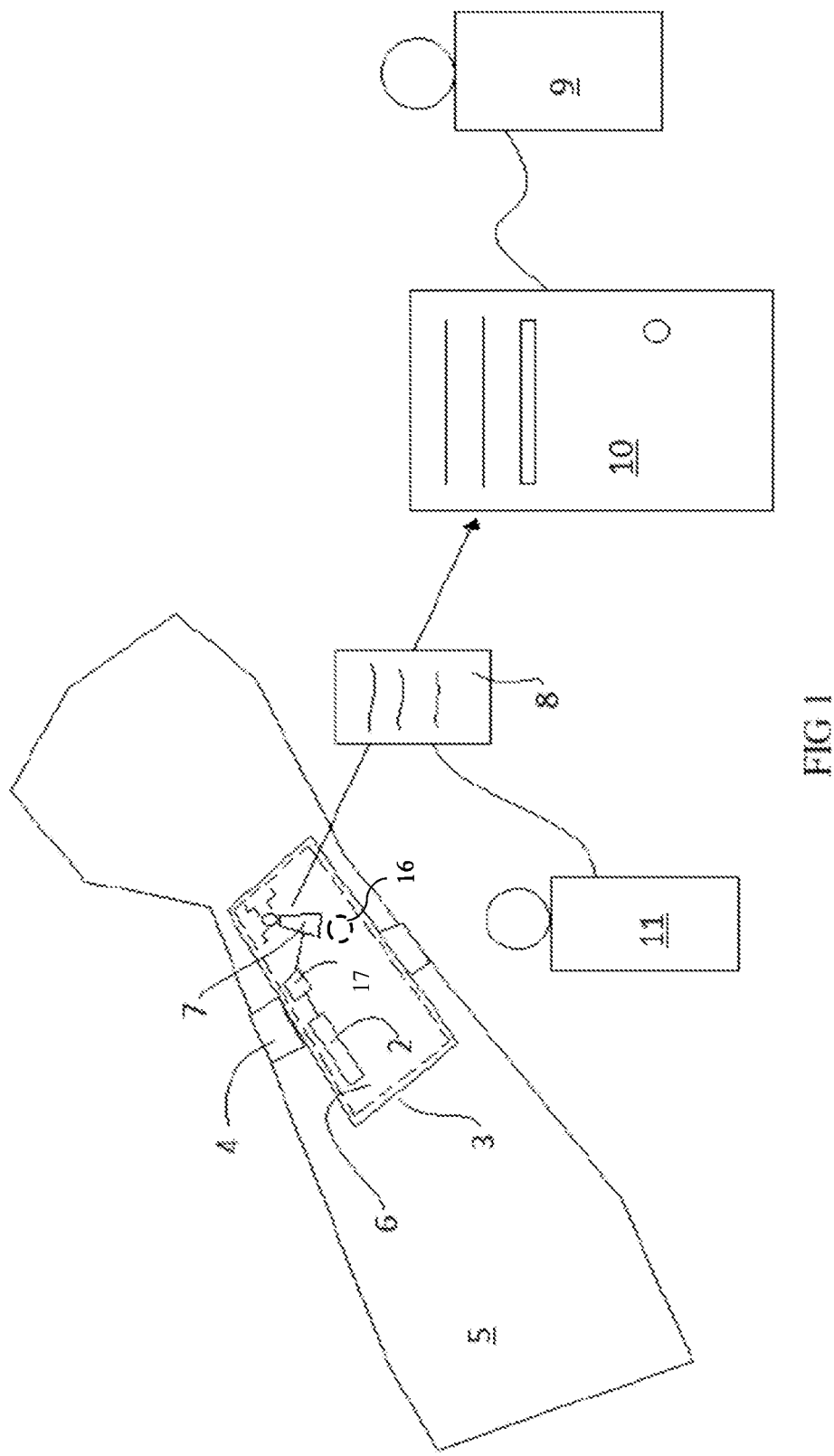
FIG. 1 is a schematic representation of the Wearable Mood and Activity Monitoring System of the present invention.
Figure 2:
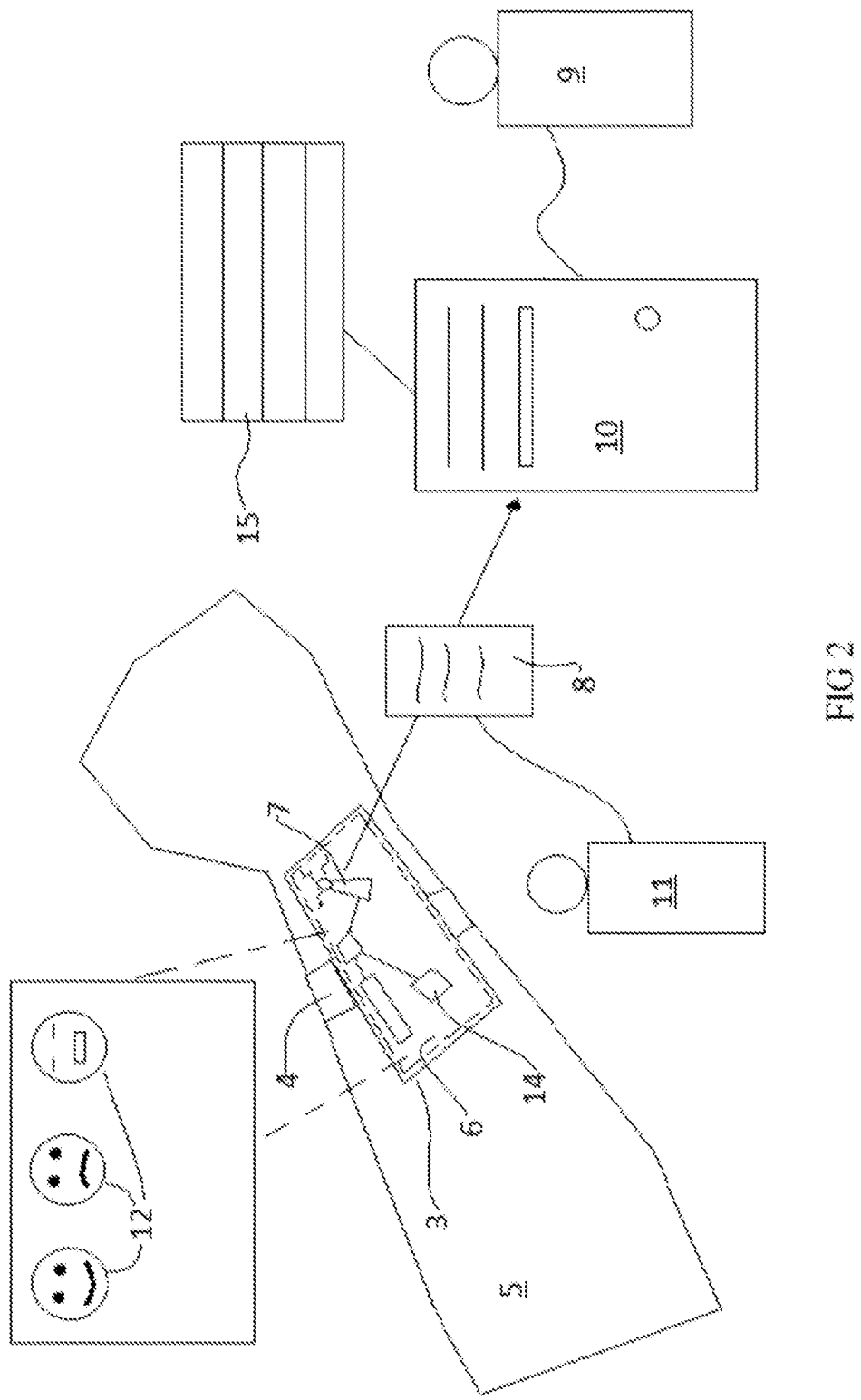
FIG. 2 is a schematic representation of pictographs of human emotions for the Wearable Mood and Activity Monitoring System of the present invention.

As shown in FIGS. 1 and 2, the present invention discloses a wearable mood and activity monitoring system configured to monitor an overall mental health of a user comprising a wrist worn device 1, further comprising an adjustable wrist band 4 and a health monitoring assembly 3, and a remote monitoring device 10. The health monitoring assembly 3 preferably further comprises in functional combination a faceplate further comprising an interactive touchscreen display 6, a microchip processor 2 in wired communication via a plurality of circuitry cables with at least one health sensor 16 for detecting real-time physiological data of said user 11, at least one accelerometer 14, at least one tracking system for tracking a relative location of said user 11, at least one information receiver and transmitter unit 7, and at least one power source 17. The health monitoring assembly 1 is preferably configured to couple to a backplate using at least one plate securer. The at least one power source 17 preferably powers the health monitoring assembly 3.

The at least one power source 17 is preferably a small watch-type lithium ion battery, however other types of batteries may be used without limitation. Alternately preferably, the at least one power source 17 is at least one solar cell configured to capture sunlight energy and use it to power the at least one health monitoring assembly.

As further shown in FIGS. 1 and 2, the user 11 preferably provides an input using the interactive touchscreen display 6 to select a user-reported mood. Additionally, the at least one health sensor 16 is preferably installed to the backplate such that the at least one health sensor 16 is preferably in contact with a radial artery of the user 11 for generating the real-time physiological data. The microchip processor 2 is preferably configured to evaluate and analyze the real-time physiological data with the user-reported mood to provide an overall mental health of the user 11. The at least one remote monitoring device 10 is preferably configured to automatically receive the real-time physiological data, the user-reported mood, and the overall mental health transmitted by the transmitter and receiving unit 7 for alerting a care provider 9 of the overall mental health of the user.

As further shown in FIG. 1, the wrist worn device 1 preferably further comprises a clock processor to track current time data. The clock processor is preferably a part of the microchip processor 2. In an alternate embodiment, the wrist worn device 1 is preferably waterproof via a watertight seal located between the backplate and the faceplate of the health monitoring assembly 3.

As further shown in FIG. 2, in an alternate embodiment the health monitoring assembly 3 is preferably configured to allow the user 11 to select a user-reported mood by using the interactive touchscreen display 6. The user-reported mood is preferably selected using a plurality of pictographs 12 depicting various moods displayed on the interactive touchscreen display 6. In an alternate embodiment, the health monitoring assembly 3 is configured to prompt the user 11 to input a user-reported mood based on the physiological data collected by the health sensor 16. To encourage the behavior of inputting data (e.g. mood, activity, sleep), users will receive prompts on a variable-interval schedule. Fixed-interval schedules will be used to reinforce behaviors immediately following data input and at the end of the day. The prompts will be paired with positive reinforcement appropriate to the data received.

Figure 3:
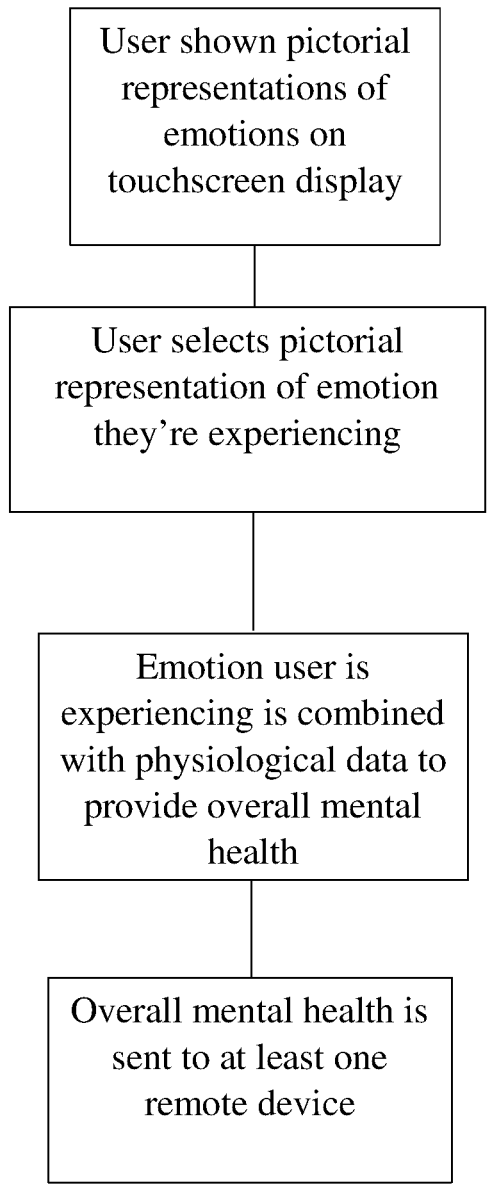
FIG. 3 is a flow chart representation of the method for allowing the user to report their mood for the Wearable Mood and Activity Monitoring System of the present invention.

As shown in FIG. 3, the microchip processor 2 preferably further comprises a data-processing means configured to combine the user-reported mood with the physiological data to communicate with the caregiver 9 and to output an overall mental health of the user 11 to the caregiver 9 via the remote monitoring device 10. The data-processing means is preferably an algorithm. For example, the algorithm may output the overall metal health of the user as a daily balance score by combining the user-reported mood input, the hours of sleep of the user, and the minutes of daily activity of the user. In this example, the hours of sleep of the user and the user's total minutes of daily activity may be additional user-reported inputs, or they may be physiological data collected by at least one health sensor contacting the user's radial artery and using real-time physiological data to determine the physiological data for the day. Alternately preferably, the data-processing means is a software program configured to accept the user-reported mood and the physiological data, analyze both the user-reported mood and the physiological data, compare the user-reported mood and the physiological data, and provide an overall mental health output. Additionally, the data processing means preferably combines the user-reported mood with the physiological data to output feedback and instructions to the user 11 via the interactive touchscreen display 6. The caregiver 9 is preferably any one of a family member, supervisor, guardian, physician, counselor, or other person in charge of monitoring the user.

As further shown in FIG. 1, the wrist band 4 is designed to releasably attach the wrist worn device to the wrist 5 of a user 11. The wrist band 4 may use any suitable means of releasable attachment in order to accomplish this, including but not limited to hook and loop fasteners, buckle and perforation type fasteners, snap fasteners, snap buckle fasteners, and any other suitable fasteners. The wrist band 4 preferably includes a means for adjusting the circumference of the band to fit different users.

The wrist band 4 is preferably constructed from a material that is safe to be worn by users with one or more of skin allergies and skin sensitivities. Preferably these materials are constructed to avoid trapping moisture against the skin of the user. Preferably these materials are further selected to avoid one or more of common skin allergies to materials and common skin sensitivities to materials. These materials may be selected to avoid inclusion of one or more of metals, latex, spandex, lycra, nylon, clothing dyes, P-phenylenediamine, phenol, formaldehyde, Colophony, chromium, and irritating curing agents including but not limited to isocyanates. In one preferred variation, the wrist band 4 is constructed from dye-free, untreated natural fibers. In another preferred variation the wrist band 4 is constructed from medical grade silicone rubber and textured to avoid trapping moisture. In this preferred variation the surface of the band may be textured to prevent significant areas of skin contact with smooth, flat material. In this preferred variation the surface of the wrist band 4 is textured with a number of high points and low points in a pattern that allows airflow and prevents continuous contact over a significant area of skin. In this preferred variation, perforations through the wrist band 4 may also be included to promote airflow to the skin of the user. The wrist band 4 may, however, be constructed of any suitable material.

The health monitoring assembly 3 is preferably constructed of a polymer material. In another preferred variation, the health monitoring assembly 3 may be constructed of a metal such as aluminum. Preferably the bottom of the health monitoring assembly 3 housing has a material attached to it that is safe for wearing by users 11 with one or more of skin sensitivities and skin allergies, including but not limited to the materials discussed above. In another preferred variation, the health monitoring assembly 3 housing is made of materials safe for those with skin sensitivities. The health monitoring assembly 3 housing may, however, be constructed of any suitable material.

In a preferred variation, one or more caregivers 9 which can be made up of parents, teachers, doctors, counselors, other family members, and other supervisors, can track and analyze data related to the user's 11 mental health and physiological data in order to better care for the overall mental health of the user 11. The health monitoring assembly 3 is configured to transmit to at least one remote device 10 that is preferably monitored by a caregiver 9 of the user 11. The health monitoring assembly 3 device may, however, transmit any suitable data used for any suitable purpose by any suitable individuals.

As further shown in FIG. 2, the microchip processor 2 preferably shows the user 11 a prompt on the interactive touchscreen display 6 where the prompt 13 allows the user 11 to select one or more pictorial representation 12 of emotions the user 11 is feeling. Preferably the pictorial representations 12 depict human emotions in an illustrated form. In one preferred variation, the pictorial representations 12 depict illustrated human faces showing emotions that the user 11 is likely to one or more of inherently recognize and learn easily.

As shown in FIG. 3, the at least one user-reported mood selected by the user 11 is preferably stored in the health monitoring assembly 3 or transmitted to a remote device 10. In one preferred embodiment, the user-reported mood selected by the user 11 is transmitted to the remote device 10 for review by at least one caregiver 9 of the user 11. In another preferred embodiment, the user-reported mood selected by the user 11 can be stored on the health monitoring assembly 3 for later access.

In an alternate embodiment, an external device may be plugged into the wrist worn device 1 by any suitable means, which can include, but is not limited to, a USB cable. Alternately preferably, an external device may be wirelessly connected to the wrist worn device 1 to access the data stored in the health monitoring assembly 3, including but not limited to at least one user-reported mood. In an alternate embodiment, one or more of the wrist worn device 1 and the remote device 10 may perform a statistical analysis on two or more user-reported moods that the user 11 selects over time. In this alternate embodiment, the statistical analysis may be used to generate one or more of i) warnings transmitted to the remote device 10 than can be accessed by at least one caregiver 9 of the user, ii) output on the screen 6 of the device that can one or more of assist and encourage the user 11 with the goal of helping the user 11 achieve healthy emotional status, iii) challenges that the user 11 may participate in through interaction with the wrist worn device 1.

The user 11 preferably uses the interactive touchscreen display 6 to bring up the user-reported mood choices at any point in time that the user 11 desires. In another preferred variation, the wrist worn device may prompt 13 the user 11 at any suitable time to select their current user-reported mood. In another alternate embodiment, both of these features may be combined. The at least one user-reported mood may, however, be used in any suitable manner.

Figure 4:
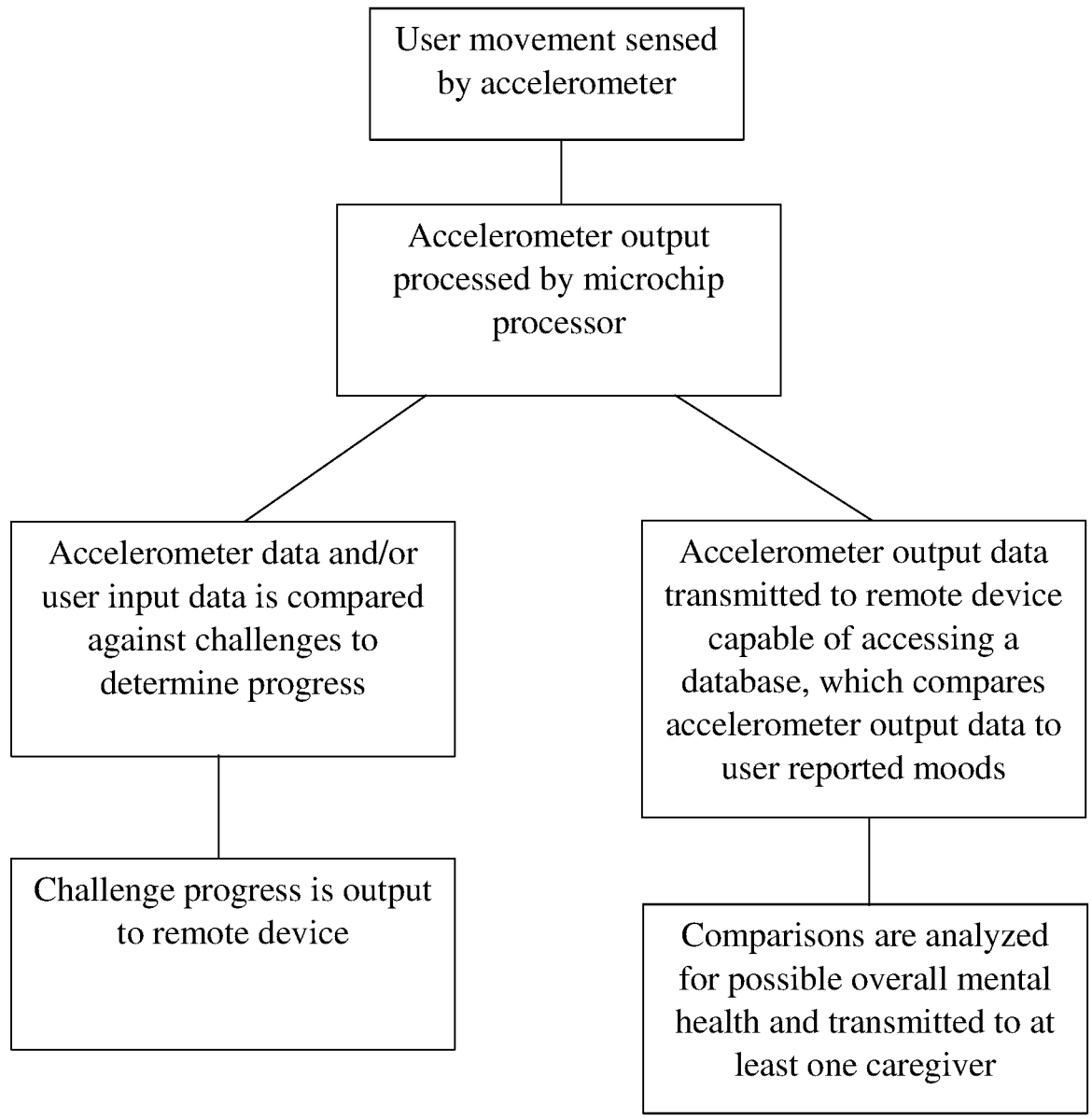
FIG. 4 is a flow chart representation of an accelerometer for the Wearable Mood and Activity Monitoring System of the present invention.

As shown in FIG. 4, in an alternate embodiment, the wrist worn device preferably gives the user 11 challenges to complete. These challenges are preferably designed to help the user 11 achieve improvements in at least one or more of A) physical health, B) mental health, C) academics, and D) athletics the user 11 participates in. One example of a challenge would be to walk or run a given certain distance over the course of the week. Another example of a challenge would be to do a certain number of push-ups in a week. Another example of a challenge would be to read a certain number of pages in a week. Another example of a challenge would be to call two friends and set up an activity to participate in. Another example of a challenge would be for the user 11 to solve a puzzle or research the answer to a question.

As further shown in FIG. 4, in the alternate embodiment explained above, the output of the accelerometer 14 is preferably used by the microchip processor 2 of the health monitoring assembly 3 to track the progress of the user 11 in accomplishing a challenge. In one alternate embodiment, the wrist worn device 1 may provide at least one or more of encouragement, aide to the user 11 to assist them in completing a challenge, feedback to the user 11 related to their progress in a challenge, and transmitted data to a remote device 10 that allows at least one caregiver 9 of the user 11 to react to the progress of the user 11 in a challenge.

The wrist worn device 1 may encourage the user 11 based on their performance, for instance telling the user 11 "Good job!" or showing the user 11 pictorial representations 12 that are encouraging or rewarding. The wrist worn device 1 may also encourage the user 11 to take certain activities that will help them complete a challenge, such as "If you walk 300 more steps today, you will complete your challenge," or "If you walk home from school today, you will complete your challenge." These messages may be in part or in whole represented pictorially and are examples only.

The wrist worn device 1 may transmit data 8 to a remote device, so that the remote device 10 can output messages or information to the at least one caregiver 9 of the user, such as "The user 11 has completed 67 pushups this week," or "The user 11 is struggling to read the number of pages in their challenge this week." The wrist worn device 1 may be configured to have the user 11 participate in any suitable challenges. The wrist worn device 1 may be configured to give the user 11 any suitable output related to their progress in challenges.

Figure 5:
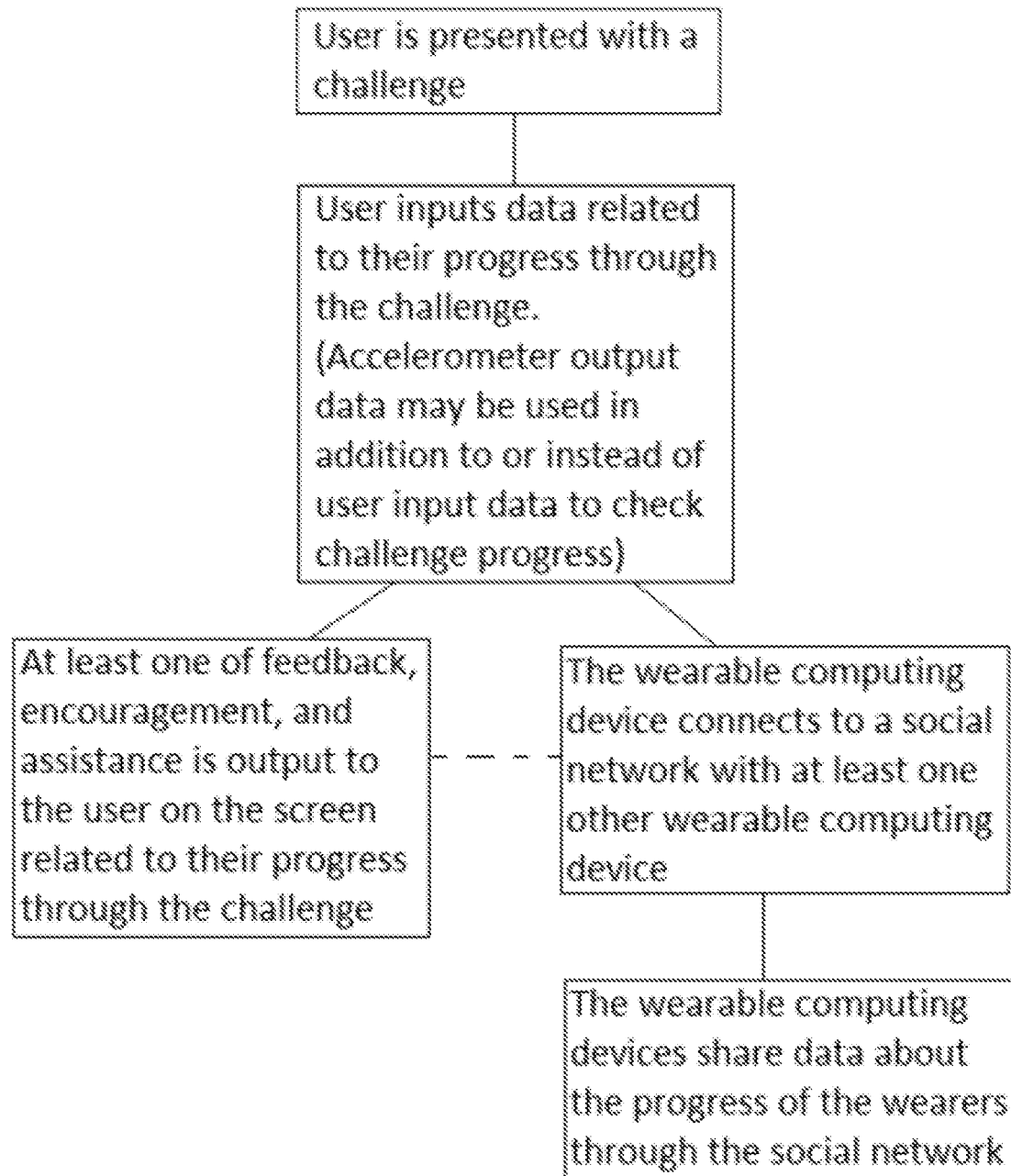
FIG. 5 is a flow chart representation related to a challenge for the Wearable Mood and Activity Monitoring System of the present invention.
Figure 6:
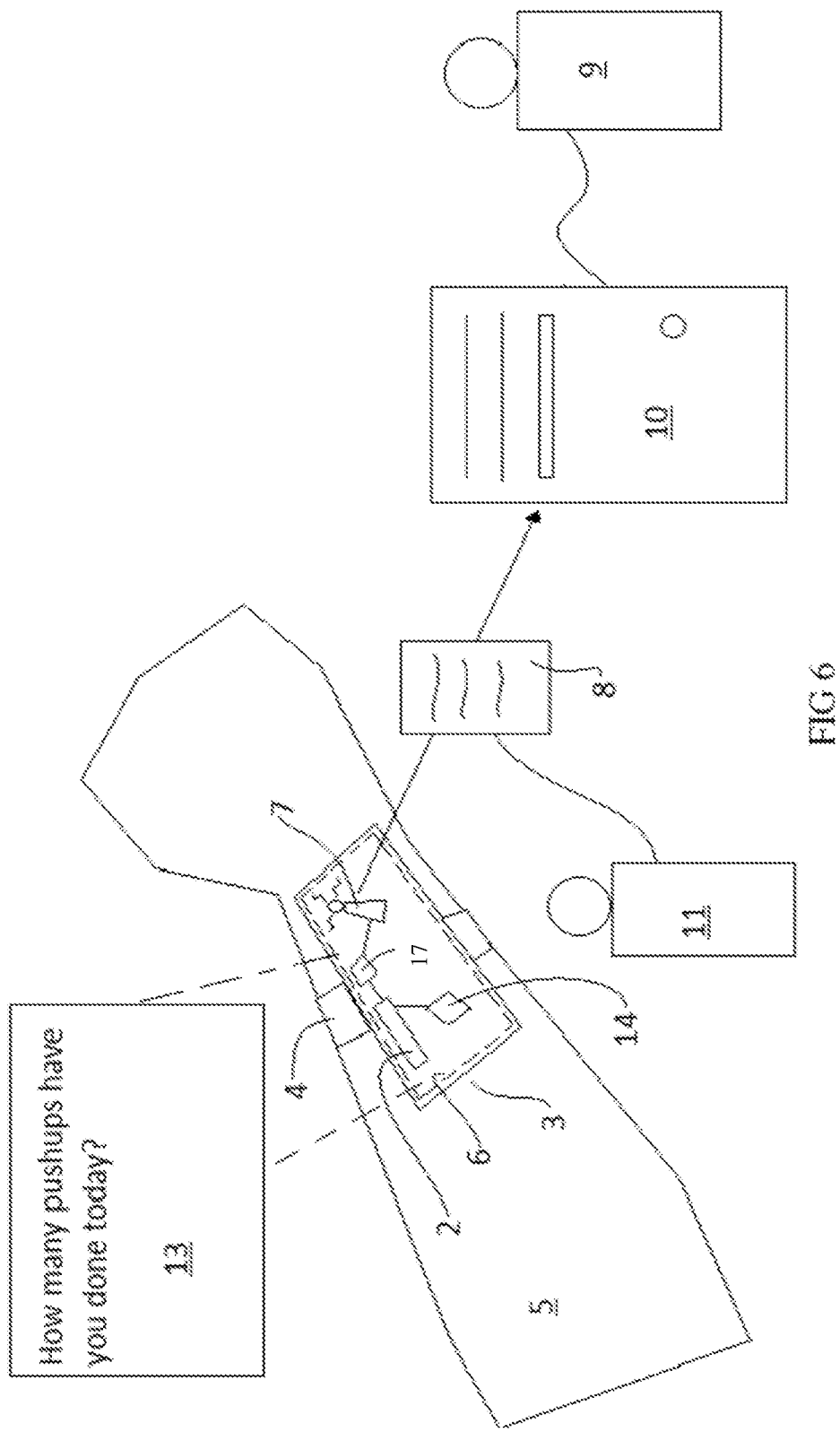
FIG. 6 is a schematic representation related to a challenge for the Wearable Mood and Activity Monitoring System of the present invention.

As shown in FIG. 5, in one preferred embodiment, the wrist worn device 1 may prompt 13 the user 11 to input information related to their progress through challenges. As shown in FIG. 6, this data may include asking the user 11 the status of their effort towards a challenge goal, for example asking a user 11 how many pushups they performed today or how many pages they read. The wrist worn device 1 may be configured to prompt 13 the user 11 for input related to their challenges in any suitable way. In an alternate embodiment, the user 11 input related to their challenges can be combined with output from the accelerometer 14 to provide two sources of data that the microchip processor 2 can use to track the progress of a user 11 in a challenge. In another variation, the wrist worn device 1 may only use data input by the user 11 to track the progress of the user 11 in a challenge. In another variation, the wrist worn device 1 may only use the output of the health sensor 16 in the wrist worn device 1 to track the progress of the user 11 in a challenge. The wrist worn device 1 may include any suitable sensors in addition to an accelerometer 14, including but not limited to magnetometers, gyroscopes, temperature sensors, heart rate monitors, GPS sensors, and any other suitable sensors.

As further shown in FIG. 5, in another alternate embodiment, the wrist worn device 1 preferably transmits data 8 to at least one remote device 10 configured to allow the wrist worn device 1 to participate in a social network with at least one other wrist worn device. In this alternate embodiment, the progress of at least two users can be shared via the social network. The users may be shown the progress of the at least one other user 11 in at least one challenge. The users may be allowed to compete against one another via the social network. The users may be allowed to play games against each other via the social network, preferably games involving real world activities resulting in benefits to one or more of 1) the physical health of the users, 2) the emotional health of the users, 3) the academics of the users, and 4) the athletics the users are involved in.

An example of the ability of the at least two users to compete via the social network would be a competition between at least two users to do the most pushups in a week. In this example, the social network might provide data from one user's wrist worn device 1 to the at least one other user, such as "user has completed 97 pushups so far this week." An example of using the social network to help the users succeed in athletics would be providing a message to the users of the social network such as "user 1 scored 3 goals in today's soccer game, congratulations user 1!" and in this example at least one other user 11 of the social network may be on the same soccer team as user 11. Challenges and data related to challenges may be used in any suitable way on the social network. In one preferred variation, the at least two users of the social network can come up with their own challenges and challenge other users of the social network to participate in the challenge they created. This preferably works with the natural tendencies of children to challenge each other and compete against each other.

Preferably the challenges can be encouraged to contain goals and processes that positively benefit the users in at least one or more of 1) the physical health of the users, 2) the emotional health of the users, 3) the academics of the users, and 4) the athletics the users are involved in. In one preferred variation, the at least two users may be provided with means for sending encouraging messages to one another over the social network. The social network may, however, be used in any suitable manner. The system of the preferred embodiments may, however, not be linked to a social network at all.

As shown in FIG. 4, the wearable computing device may output data from sensors to a remote device 10 capable of accessing a remote database 15, and capable of carrying out statistical analysis on the transmitted sensor data. The transmitted sensor data may include but is not limited to accelerometer 14 data, physiological data recorded by the health sensor 16, time data corresponding to the sensor data, and any other suitable sensor data. In another preferred variation, the transmitted data may also include data from user 11 inputs, which can include at least one emotional state the user 11 has input, and any other suitable data the user 11 may input.

Preferably the remote monitoring device 10 is preferably configured to carry out statistical analysis on the transmitted data and access a database that includes at least data on conditions related to one or more of physical health and mental health. In another preferred variation, the microchip processor 2 on the wrist worn device 1 performs statistical analysis on the data taken over time by the health monitoring assembly 3 and sends the statistical analysis to the remote monitoring device 10 that is preferably configured to access a database that includes at least data on conditions related to one or more of physical health and mental health.

The remote monitoring device 10 can preferably use pattern matching algorithms to determine conditions the user 11 is statistically likely to have based on the statistical analysis of the transmitted data. The system preferably can send information related to these possible conditions the user 11 may have to a second remote monitoring device which can output data to at least one caregiver 9 of the user. In another preferred variation, information related to the possible conditions the user 11 may have is transmitted back to the health monitoring assembly 3, and the wrist worn device 1 can perform one or more actions including but not limited to outputting data on the conditions to the user, prompting the user 11 with challenges that may improve the possible conditions the user 11 may be suffering, creating actions in the social network that may improve the possible conditions the user 11 may be suffering, prompting the user 11 to perform actions that may improve the possible conditions the user 11 may be suffering.

In one preferred variation, the health monitoring assembly 3 tracks physical activity levels and sleep patterns of the user 11 and transmits at least this data to the remote monitoring device 10 that is preferably configured to perform statistical analysis and access a database with information relating to conditions a user 11 may suffer. The health monitoring assembly 3 may, track any suitable activities and transmit any suitable data for identifying conditions the user 11 may suffer from.

In another preferred variation, the software on the health monitoring assembly 3 is preferably configured to perform statistical analysis of sensor data and compare the analysis results to at least one database that is at least one of A) stored on computer readable memory and B) accessible by data transmission over the transmitter and receiver unit 6, where the software utilizes the microchip processor 2 to compare data from the at least one database and the statistical analysis to identify conditions the user 11 may suffer within the wrist worn device 1. In one preferred variation, at least one of the wrist worn device 1 and the remote monitoring device 10 is preferably configured to access a remote database 15 and utilize the data on the conditions the user 11 may suffer to access articles in a database related to the conditions the user 11 may suffer. Then at least one of the wrist worn device 1 and the remote monitoring device 10 is configured to access the remote database 15 and transmit one or more articles related to the conditions the user 11 may suffer, if any are located, to a remote monitoring device 10 that can be accessed by at least one caregiver 9. Preferably the at least one article is transmitted to a remote monitoring device 10 so that at least one caregiver 9 of the user 11 can read information related to conditions that have been identified that the user 11 may suffer. These articles may include scientific research articles, popular publication articles, or any suitable article from any suitable source with information related to the conditions identified that the user 11 may suffer. Preferably the at least one caregiver 9 can opt out of receiving articles related to potential conditions the user 11 may suffer.

In one preferred variation, the health monitoring assembly 3 can track data points over time and provide the data in a format for viewing on the wrist worn device 1 and a separate computing device which can receive data from the wrist worn device 1. In this variation the data is preferably displayed in formats useful for representing data over time, including but not limited to graphs, tables, charts, journal formats, and any other suitable format for viewing data represented over time. This preferably allows the user 11 and/or the caregiver 9 of the user 11 to track the progress of the user 11 in any suitable category over time.

Preferably as much of the output provided to the user 11 as possible is provided in pictorial representations 12. In one preferred variation, the wrist worn device 1 may provide alarm reminders to the user 11. In one example, the wrist worn device may trigger an alarm and display a picture of a pill to remind a user 11 to take medication. In another example, the wrist worn device 1 may show a pictorial representation 12 of a test to remind the user 11 they have a test coming up. The users of the device are preferably intended to be at least one of children and the developmentally disabled, so making as many outputs of the device as possible in easy-to-understand pictorial representations 12 benefits these users. The wrist worn device 1 may, however, provide any suitable reminders and alarms. The wrist worn device 1 may, however, represent information to the user 11 in any suitable manner.

In an alternate embodiment, the wrist worn device 1 preferably provides positive reinforcement for activities the user 11 carries out that can benefit the user 11. Preferably, the positive reinforcement is given irregularly, as irregular reinforcement is psychologically more effective in motivating the user 11. The wrist worn device 1 may, however, provide any suitable reinforcement in any suitable manner.

In a preferred embodiment, the wrist worn device 1 preferably further comprises a tracking system, such as a GPS location sensing chipset, preferably configured to determine the location of the wrist worn device 1. In this preferred embodiment, the wrist worn device 1 transmits its location to at least one remote monitoring device 10. At least one second wrist worn device also transmits its location to the social network. If the at least one wrist worn device 1 and the at least one remote device 10 determines that another wrist worn device is nearby, it may alarm the user. The alarm may vibrate and display an image of the user 11 of the at least one additional wrist worn device 1. In this preferred variation, the at least two wrist worn devices may share data through the social network, where the data 8 may include location, activity data, sports data, social data, data on challenges the user 11 may be participating in, and any other suitable data. The data 8 may be at least one of shared with and downloaded by one or more of friends, caregivers 9, teammates, coaches, and any other suitable parties. The wrist worn device 1 may share any suitable data with nearby wearable computing devices. The wrist worn device may, however, have any suitable means for detecting its location.

Although the present invention has been described by way of example, it should be appreciated that variations and modifications may be made without departing from the scope of the invention. Furthermore, where known equivalents exist to specific features, such equivalents are incorporated as if specifically referred to in this specification.

We claim:

1. A health monitoring system comprising: a wrist worn device and a remote monitoring device, wherein the wrist worn device comprises: an adjustable wrist band configured to attach to a wrist of a user; a health monitoring assembly comprising, in functional combination, a faceplate including an interactive touchscreen display; a microchip processor in wired communication via a plurality of circuitry cables with at least one health sensor configured to detect real-time physiological data of the user;
   at least one accelerometer;
   at least one tracking system configured to track a relative location of the user;
   at least one information receiver and transmitter unit; and
   at least one power source;
   wherein the health monitoring assembly is configured to couple to a backplate using at least one plate securer;
   wherein the at least one health sensor is installed to the backplate and configured to contact a radial artery of the user from which the at least one health sensor detects the real-time physiological data;
   wherein the health monitoring assembly is further configured to prompt the user to select a user-reported mood input by using the interactive touchscreen display;
   wherein the at least one microchip processor comprises a data processing means for evaluating the real-tiome physiological data and the user-reported mood to provide an overall mental health of the user; and
   wherein the at least one remote monitoring device is configured to receive the user-reported mood and the real-time physiological data to alert a care provider of the overall mental health of the user; and
   wherein the caregiver is able to input at least one instruction or feedback to the user into the remote monitoring device which is configured to send the at least one instruction or feedback to the health monitoring assembly.

2. The health monitoring system of claim 1, wherein the wrist worn device further comprises a clock processor configured to track current time data.

3. The health monitoring system of claim 1, wherein the prompt is based on the real-time physiological data.

4. The health monitoring system of claim 1, wherein the wrist worn device is waterproof and comprises a watertight seal located between the backplate and the faceplate.

5. The health monitoring system of claim 1, wherein the user-reported mood input is selected using a plurality of pictographs and pictorials depicting various moods displayed on the interactive touchscreen display.

6. The health monitoring system of claim 1, wherein the data processing means is configured to combine the user-reported mood input with the physiological data to communicate with the caregiver using trends over time.

7. The health monitoring system of claim 6, wherein the user-reported mood input is combined with the real-time physiological data to output feedback and instructions to the caregiver.

8. The health monitoring system of claim 6, wherein the user-reported mood input is combined with the real-time physiological data to output feedback and instructions to the user.

9. The health monitoring system of claim 1, wherein the health monitoring assembly is configured to provide a challenge to the user.

10. The wearable mood and activity monitoring system of claim 9, wherein the wrist worn device further comprises a clock processor configured to track current time data.

11. A wearable mood and activity monitoring system comprising:
 a wrist worn device comprising an adjustable wrist band configured to attach to a wrist of a user, a health monitoring assembly comprising in functional combination a faceplate including a user interface, a microchip processor in wired communication via a plurality of circuitry cables with at least one health sensor configured to detect real-time physiological data of the user, at least one accelerometer, at least one tracking system configured to track a relative location of the user, at least one information receiver and transmitter unit, and at least one power source; wherein the user interface comprises an interactive touchscreen display and is configured to prompt the user to input a user-reported mood as selected through the interactive touchscreen display, wherein the user-reported mood is represented by a plurality of pictographs;
 wherein the health monitoring assembly is configured to couple to a backplate using at least one plate securer;
 wherein the at least one health sensor is installed to the backplate and configured to contact a radial artery of the user from which the at least one health sensor detects the real-time pysiological data;
 wherein the at least one microchip processor comprises a data processing means configured to evaluate the real-time physiological data and the user-reported mood and to provide an overall mental health of the user; and
 wherein the data processing means is further configured to output at least one instruction or feedback to the user for improving the overall mental health;
 wherein the caregiver is able to input at least one instruction or feedback to the user into the remote monitoring device which is configured to send the at least one instruction or feedback to the health monitoring assembly.

12. The wearable mood and activity monitoring system of claim 11, wherein the wrist worn device is waterproof and comprises a watertight seal located between the backplate and the faceplate.

13. The wearable mood and activity monitoring system of claim 11, further comprising a remote monitoring device configured to receive transmissions from the health monitoring assembly.

14. The wearable mood and activity monitoring system of claim 13, wherein the remote monitoring device is configured to notify a caregiver of the user-reported mood, the real-time physiological data, and the overall mental health.

15. The wearable mood and activity monitoring system of claim 13, wherein the data processing means is configured to combine the user-reported mood with the real-time physiological data and to output caregiver feedback or instructions to the caregiver based thereupon.

16. The wearable mood and activity monitoring system of claim 13, wherein the data processing means is configured to combine the user reported mood with the real-time physiological data to output the at least one instruction or feedback to the user based thereupon.

17. The wearable mood and activity monitoring system of claim 13, wherein the caregiver is able to input a challenge for the user and the remote monitoring device is configured to send the challenge to the health monitoring assembly, wherein the health monitoring assembly is configured to alert the user of the challenge.

18. The wearable mood and activity monitoring system of claim 11, wherein the health monitoring assembly is configured to provide a challenge to the user via the interactive touchscreen display.

19. The wearable mood and activity monitoring system of claim 11, wherein the health monitoring system is configured to present the user with the at least one instruction or feedback in pictorial or pictographic representations which are easily understandable.

* * * * *